United States Patent [19]

Imamura et al.

[11] Patent Number: 5,238,816

[45] Date of Patent: Aug. 24, 1993

[54] OMEGA CARBOXYALCOHOL OXIDASE ENZYME

[75] Inventors: Shigeyuki Imamura; Naoki Muto; Kenya Ishizawa, all of Shizuoka, Japan

[73] Assignee: Asahi Kasei Kogyo Kabushiki Kaisha, Osaka, Japan

[21] Appl. No.: 788,299

[22] Filed: Nov. 5, 1991

Related U.S. Application Data

[62] Division of Ser. No. 570,591, Aug. 21, 1990, Pat. No. 5,171,681.

[51] Int. Cl.$^5$ .......................... C12Q 1/28; C12P 7/00; C12P 7/64; C12P 7/40
[52] U.S. Cl. .................................. 435/28; 435/132; 435/134; 435/136
[58] Field of Search ................ 435/28, 132, 134, 136

[56] References Cited

U.S. PATENT DOCUMENTS

| | | | |
|---|---|---|---|
| 3,884,764 | 5/1975 | Goodhue | 195/103.5 R |
| 3,907,642 | 9/1975 | Richmond | 195/62 |
| 3,907,645 | 9/1975 | Richmond | 195/103.5 R |
| 3,909,359 | 9/1975 | Goodhue | 195/66 R |
| 4,003,794 | 1/1977 | Sugiura | 195/66 R |
| 4,008,127 | 2/1977 | Gruber | 195/65 |
| 4,035,237 | 7/1977 | Masurekar | 195/66 R |
| 4,043,870 | 8/1977 | Evans | 195/66 R |
| 4,061,540 | 12/1977 | Yoshida | 195/62 |
| 4,093,517 | 6/1978 | Masurekar | 195/66 R |
| 4,101,381 | 7/1978 | Klose | 195/99 |
| 4,102,742 | 7/1978 | Klose | 195/103.5 R |
| 4,144,129 | 3/1979 | Gruber | 195/66 R |
| 4,186,251 | 1/1980 | Tarbutton | 435/11 |
| 4,334,023 | 6/1982 | Gauhl | 435/190 |
| 4,349,633 | 9/1982 | Worne | 435/281 |
| 4,374,930 | 2/1983 | Snoke | 435/190 |
| 4,425,435 | 1/1984 | Matsui | 435/190 |
| 4,540,668 | 9/1985 | Hopkins | 435/190 |
| 4,619,898 | 10/1986 | Hopkins | 435/190 |
| 5,010,005 | 4/1991 | Duff | 435/147 |

FOREIGN PATENT DOCUMENTS

| | | |
|---|---|---|
| 81878 | 6/1983 | European Pat. Off. . |
| 249282 | 9/1987 | Fed. Rep. of Germany . |
| 4140791 | 11/1979 | Japan . |
| 8107175 | 6/1983 | Japan . |
| 8129973 | 8/1983 | Japan . |
| 0062980 | 4/1985 | Japan . |
| 0259184 | 12/1985 | Japan . |
| 1096986 | 5/1986 | Japan . |
| 3198984 | 8/1988 | Japan . |
| 761553 | 9/1980 | U.S.S.R. . |

OTHER PUBLICATIONS

Janssen F. W., Alcohol Oxidase, A Flavoprotein ... Biochim et Biophys, 151 1968 330-342.
Janssen F. W., Alcohol Oxidase, A Novel Enzyme ... Biochem & Biophysical Rsch Com 20, 5, 1965 630-5.
Tani Y. The Microbial Metabolism of Methanol ... Agr Biol Chem vol. 36 1 1972 68-75.
Fujii T., Oxidation of Methanol, Formaldehyde ... Agr Biol Chem vol. 36 13 2297-2306 1972.
Mitz, M. A., Omega Hydroxy Fatty Acid Dehydrogenase, Biochim et Biophysic., 46 1961 45-50.

(List continued on next page.)

Primary Examiner—Michael G. Wityshyn
Assistant Examiner—Ralph Gitomer
Attorney, Agent, or Firm—Young & Thompson

[57] ABSTRACT

A novel ω-carboxyalcohol oxidase catalyzes at least one of the following reactions:

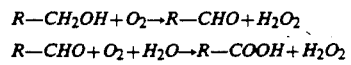

wherein R is alkyl, alkenyl, ω-carboxyalkyl or ω-carboxyalkenyl. The enzyme has substrate specificity on at least 12-hydroxydodecanoic acid, 1-dodecanol, 1-decanol, 1-octanol and 1-hexanol, and has no substrate specificity on methanol, ethanol or glycerol. The enzyme does not require the presence of NAD or NADP for its use. Also disclosed is a process for producing the enzyme, an assay method for substrates of the enzyme, and a process for producing carboxylic acid employing the enzyme.

2 Claims, 5 Drawing Sheets

OTHER PUBLICATIONS

Sahm, H., Microbial Assimilation of Methanol Eur J. Biochem 36 250–256 1973.

Kato N., Alcohol Oxidases of Kloeckera SP . . . Eur J. Biochem 64 341–350 1976.

Kolattukudy P. G. W-Hydroxy Fatty Acid: NADP . . . Methods in Enzymology 71 1981 411–420.

Ratledge C., Microbial Conversions of Alkanes . . . J of Am Oil Chem Soc 61 2 1984 447–453.

Kemp, G. D. et al. "Inducible Long Chain Alcohol Oxidase . . . " *Appl Microbiol Biotechnol* 29:370–374, 1988.

Blasig, R. et al., "Degradation of Long-Chain n-Alkanes" *Appl Microbiol Biotechnol* 28:589–597.

OMEGA CARBOXYALCOHOL OXIDASE ENZYME

This application is a division of copending application Ser. No. 07/590,591, filed Aug. 21, 1990, now U.S. Pat. No. 5,171,681, issued Dec. 15, 1992.

BACKGROUND OF THE INVENTION

1. Field of the Invention

This invention relates to a novel ω-carboxyalcohol oxidase, a process for its production, a method for detecting aliphatic alcohols, aliphatic aldehydes or ω-carboxylic acid derivatives thereof using the novel ω-carboxyalcohol oxidase, and a process for producing carboxylic acid using the said ω-carboxyalcohol oxidase. More particularly the present invention relates to a novel ω-carboxyalcohol oxidase having the following biochemical properties.

1. Enzymatic action: catalyzing at least one of the following reactions a) and b)

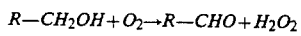

$$R-CH_2OH + O_2 \rightarrow R-CHO + H_2O_2 \quad \text{a)}$$

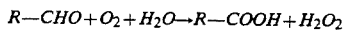

$$R-CHO + O_2 + H_2O \rightarrow R-COOH + H_2O_2 \quad \text{b)}$$

wherein R—CH$_2$OH is an aliphatic alcohol or a corresponding ω-carboxylic acid derivative, except methanol and ethanol, R—CHO is the corresponding aliphatic aldehyde or its ω-carboxylic acid derivative, and R—COOH is the oxidized form of R—CHO.

2. Substrate specificity: having substrate specificity on at least HO$_2$C—(CH$_2$)$_{11}$—OH, H$_3$C—(CH$_2$)$_{11}$—OH, H$_3$C—(CH$_2$)$_9$—OH, H$_3$C—(CH$_2$)$_7$—OH and H$_3$C—(CH$_2$)$_5$—OH, and having no substrate specificity on methanol, ethanol or glycerol.

3. Utilization of coenzyme: no utilization of NAD and NADP.

2. Description of the Prior Art

The hitherto-known oxidase having substrate specificity for aliphatic acids is alcohol oxidase (EC.1.1.3.13) which catalyzes the following reaction to form aldehyde.

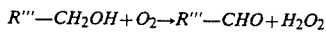

$$R'''—CH_2OH + O_2 \rightarrow R'''—CHO + H_2O_2$$

Alcohol oxidase from *Basidiomycete* (*Biochim. Biophys. Acta*, 151: 330-342 (1968), *Biochem. Biophys. Res. Commun.*, 20: 630-634 (1965)), *H. polymorpha*, a yeast grown in methanol, and *Kloeckera* sp. (*Agr. Biol. Chem.*, 36: 2297-2306 (1972), *Eur. J. Biochem.*, 36: 250-256 (1973), ibid., 64: 341-350 (1976), *Agr. Biol. Chem.*, 36: 68-75 (1972)) are known. Alcohol oxidase from Basidiomycete has substrate (R'''—CH$_2$OH) specificity for C$_{2-4}$ straight chain primary alcohol, allylalcohol or 2-propione-1-o1. Alcohol oxidase from *H. polymorpha* has substrate specificity for C$_{1-4}$ straight chain primary alcohol, 2-propene-1-o1 or 2-butene-1-o1, and alcohol oxidase from *Kloeckera* sp. has substrate specificity for C$_{1-4}$ straight chain primary alcohol, 2-propene-1-o1, 2-butene-1-o1 or allylalcohol.

Hence, alcohol oxidase from these origins generates aldehyde and has substrate specificity, at least as regards straight chain primary alcohol, for lower aliphatic alcohol or C$_4$ and below.

Further, enzymes having substrate specificity for glycerol, e.g. glycerol dehydrogenase or glycerol-2-dehydrogenase (EC.1.1.1.6, EC.1.1.1.72, EC.1.1.1.156) and glycerol oxidase are known. These enzymes oxidize glycerol and generate dihydroacetone or glyceroaldehyde, and have no activity for catalyzing a reaction which generates a carboxylic acid derivative.

There is also known an oxidase which has substrate specificity for fatty acids having an ω-hydroxy group (such compounds may also be referred to as aliphatic alcohols having an ω-carboxy group, hereinafter designated ω-carboxyalcohols), and which oxidizes the said substrate to generate dibasic acid. The enzyme is known from animal tissue (*Biochim. Biophys. Acta.*, 46: 45–50 (1961)) as well as from plant tissue (*Methods in Enzymology*, Vol. 71: pp. 411–420, 1981). These enzymes require the presence of coenzyme NAD or NADP to be active.

As hereinabove reviewed, prior known alcohol oxidases have substrate specificities for lower alcohols of C$_4$ and below, at least as regards straight chain aliphatic primary or secondary alcohol, for glycerol, or for e-hydroxy carboxylic acid in the presence of coenzyme NAD or NADP. An enzyme which does not require coenzyme, has no substrate specificity for straight chain primary alcohol of C$_2$ and below, and requires oxygen to generate hydrogen peroxide, has never been known.

SUMMARY AND OBJECTS OF THE INVENTION

We have found that Streptomyces strain AC 8205 isolated from a soil sample from a field in Sumoto-shi, Hyogoken, Japan, produces an ω-carboxyalcohol oxidase enzyme, and we have isolated and purified the said enzyme, then completed a novel method for production of carboxylic acid using the said enzyme.

The said enzyme has found to be a novel enzyme in view of its enzymatic action, substrate specificity and utilization of coenzyme, and has been designated ω-carboxyalcohol oxidase.

An object of the present invention is to provide a novel enzyme ω-carboxyalcohol oxidase having the biochemical properties described hereinafter.

Another object of the present invention is to provide a process for producing ω-carboxyalcohol oxidase which comprises culturing ω-carboxyalcohol oxidase-producing microorganisms belonging to the genus Streptomyces in a culture medium, and isolating ω-carboxyalcohol oxidase therefrom.

The present invention thus provides a novel enzyme, ω-carboxyalcohol oxidase. The enzyme is useful for analysis and assay of various alcohols and as a diagnostic enzyme reagent. Further, carboxylic acid can be produced from the corresponding alcohol or aldehyde by using the enzyme of the present invention. Specifically, dibasic acid can be produced starting from ω-carboxylic acids of aliphatic alcohol or aldehyde. Among dibasic acids, C$_{6-15}$ dibasic acids can be used as a raw material, for example, monomers of plastics polymers, synthetic fibers such as nylon, anti-freezes, plasticizers and lubricants. Examples are brassilic acid and pentadecanedioic acid, the former of which may be esterified to prepare polyester or amidated to produce polyamide, compounds useful for synthetic plastics, synthetic lubricants, plasticizers or perfumes, and the latter of which may be used as a raw material of the neutral perfume cyclopentadecanone. These materials are difficult to produce by chemical synthesis at a low cost, and the present invention thus provides a useful production process.

Furthermore, according to an assay method for aliphatic alcohol and aliphatic aldehyde or u-carboxylic acid derivatives thereof, according to the present invention, the assay can be made quantitatively in a precise manner. Since ω-carboxylic acid derivative of aliphatic alcohol is an intermediate of ω-hydroxylated fatty acid, the assay method of the present invention is useful for assaying an intermediate metabolite of fatty acid and for screening of the enzyme in the metabolism of fatty acid.

DETAILED DISCUSSION

Figure 1:
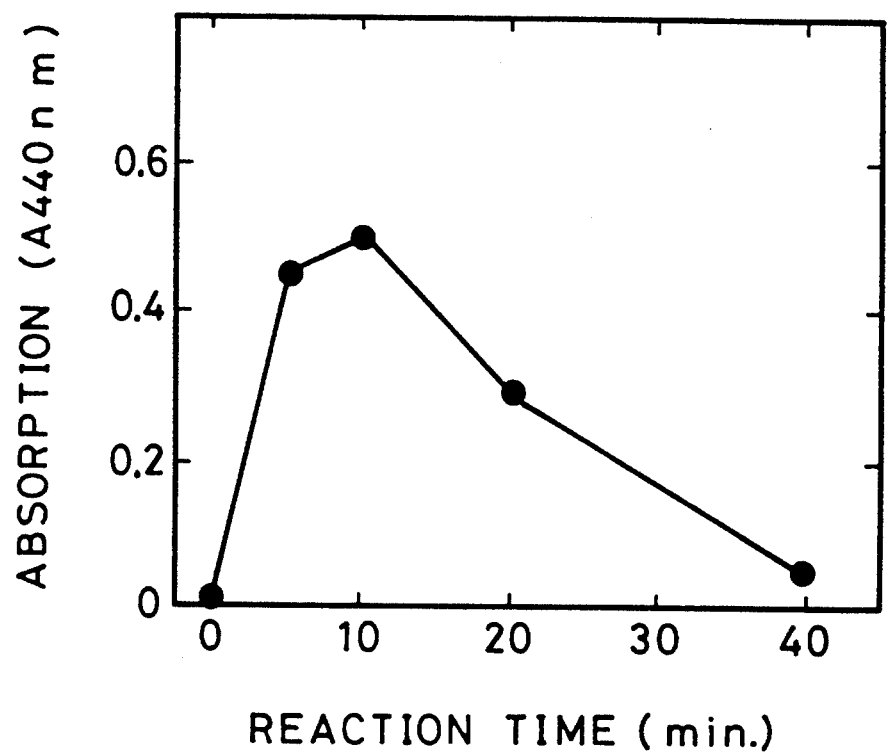
FIG. 1 is a concentration curve showing the generation and consumption of aldehyde according to the above reactions a) and b), using the enzyme according to the invention.

The taxonomic properties of the Streptomyces strain AC 8205 are as follows:

I. Morphological Properties

Morphological observations by optical microscopy and electron microscopy upon culturing on inorganic salt-starch agar medium, glycerol-asparagine agar medium or yeast extract-malt extract agar medium at 30° C. for 14 days are as follows:

The substrate mycelium is curved or straight, grown with branching, 0.3–0.5 μm in diameter and does not form fragmentation.

The aerial mycelium grown on substrate mycelium is formed with curved or straight long principal axis and short branches which are alternate or opposite, 0.4–0.6 μm in diameter. Tops of branches are loose spirals with 2–4 rounds and approximately 10–20 chain spores.

The spores are oval and 0.6–0.8×0.8–1.0 μm in size with spiny surfaces.

No sporangia, motile spores, verticillae or sclerotia are formed.

II. Composition of Diaminopimelic Acid

LL-type diaminopimelic acid is found and no meso-type is detected according to the method of Staneck et al., (*Appl. Microbiol.*, Vol. 28, pp. 226-231 (1974)).

III. Cultural Observation

Observations on various media cultured at 30° C. for 20 days are shown in Table 1.

Color indications are made by consulting the *Color Harmony Manual*, 4th Ed., 1958 (Container Corp. of America).

IV. Physiological Properties

A. Growth temperature: 20°–40° C. (optimum: 30°–37° C.)

B. Gelatin liquefaction: positive

C. Starch hydrolysis: positive

D. Skim milk:
   peptonization: positive
   coagulation: positive

E. Melanine pigment formation:
   tyrosine agar: negative
   peptone-yeast extract-iron agar: negative F. Utilization of carbon sources:
   positive L-arabinose, D-fructose, D-glucose, inositol, D-mannitol, rhamnose and D-xylose;
   negative: raffinose and sucrose.

TABLE 1

| Agar medium | Growth | Color of substrate mycelium | Aerial mycelium | Soluble pigment |
|---|---|---|---|---|
| Sucrose-nitrate | good | Bamboo (2fb) to colorless | good: Beige (3ge) to Silver Gray (3fe) | none |
| Glucose-asparagine | poor | Colorless | trace: White (a) | none |
| Glycerol-asparagine | good | Bamboo (2gc) partially Dark Brown (2nl) | good: Natural (3dc) to Oyster White (b) | none |
| Inorganic salts-starch | good | Clove Brown (3ni) | good: Beige (3ge) to Silver Gray (3fe) | none |
| Tyrosine | good | Dark Brown (3nl) | good: Natural (3dc) | Clove Brown (3ni) |
| Oatmeal | good | Bamboo (2fb) to colorless | moderate: Beige (3ge) to Silver Gray (3fe) | none |
| Yeast extract-malt extract | good | Brown (3lg) to Camel (3ni) | good: Silver Gray (3fe) to Natural (3dc) | Clove Brown (3ni) |
| Nutrien | moderate | Light Ivory (2ca) to colorless | poor: White | none |
| Bennet's | good | Camel (3ie) | good: Silver (3fe) to Natural (3dc) | Clove Brown (3ni) |
| Emerson's | good | Light wheat (2ea) to Bamboo (2fb) | moderate to poor: White (a), partially Beige (3ge) | Brown, slightly produced |

As stated above, the strain AC 8205 has the taxonomical properties of forming aerial mycelium which form spores of chains with spirals on the top from the substrate mycelium and which do not form flagellate spores or sporangia, and is thus identified as belonging to genus Streptomyces. This strain is referred to as Streptomyces sp. AC 8205, and has been deposited in The Fermentation Institute, Agency of Industrial Science and Technology, M.I.T.I., Japan as Deposit No. FERM BP-2491.

An ω-carboxyalcohol oxidase of the present invention has the following biochemical properties of enzyme action and substrate specificity.

1. Enzyme action: catalyzing at least one of the following reactions a) or b)

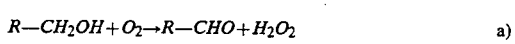

$$R-CH_2OH + O_2 \rightarrow R-CHO + H_2O_2 \qquad a)$$

$$R-CHO + O_2 + H_2O \rightarrow R-COOH + H_2O_2 \qquad b)$$

wherein R—CH$_2$OH is an aliphatic alcohol or its ω-carboxylic acid derivative, except methanol and ethanol, R—CHO is the corresponding aliphatic aldehyde or its ω-carboxylic acid derivative, and R-COOH is the oxidized form of R—CHO.

2. Substrate specificity: having substrate specificity on at least HO$_2$C—(CH$_2$)$_{11}$—OH, H$_3$C—(CH$_2$)$_{11}$—OH, H$_3$C—(CH$_2$)$_9$—OH, H$_3$C—(CH$_2$)$_7$—OH and $H_3C-(CH_2)_5-OH$, and having no substrate specificity on methanol, ethanol or glycerol.

3. Utilization of coenzyme: no utilization of NAD and NADP.

The microorganism Streptomyces sp. AC 8205 specified hereinbefore is merely illustrative of microorganisms which produce the novel ω-carboxyalcohol oxidase of the present invention, and other ω-carboxyalcohol oxidase-producing microorganisms belonging to the genus Streptomyces can be included among the microorganisms used in the present invention. Microorganism strains are easily mutated naturally or artificially, and hence these mutants which produce ω-carboxyalcohol oxidase in an isolatable amount can also be used in the present invention. Furthermore, strains which have been improved by recombinant DNA technology for such enzyme production are also to be included in the present invention.

An embodiment of the process for producing ω-carboxyalcohol oxidase by the said enzyme-producing microorganisms belonging to genus Streptomyces is as follows:

An ω-carboxyalcohol oxidase-producing microorganism belonging to genus Streptomyces is conventionally cultured in a nutrient medium for antibiotic or enzyme production. Solid or liquid culture can be used.

The nutrient sources for the microorganisms are conventional media for microorganism cultivation. As nitrogen sources, assimilable nitrogen sources, for example, corn steep liquor, soybean powder, peptone, various meat extracts, yeast extracts, ammonium sulfate or ammonium chloride can be used. As carbon sources, assimilable carbon sources such as sucrose, glucose, molasses or glycerin can be used. Furthermore, various inorganic salts such as sodium chloride, potassium chloride, magnesium sulfate, potassium phosphate or potassium dihydrogenphosphate can optionally be used.

The culturing temperature can be varied within the ranges of ω-carboxyalcohol oxidase production and microorganism growth, and is usually 20°–40° C.

The culturing time can be varied according to conditions, and is usually 50–100 hours, and the cultivation should naturally be terminated at the time of maximum production of enzyme.

The ω-carboxyalcohol oxidase of the present invention is an endo-enzyme and is included in the cells.

The ω-carboxyalcohol oxidase of the present invention can be isolated by separating the cultured cells from the cultured broth, suspending the wet cells in a buffer solution such as phosphate buffer or Tris-HCl buffer, and treating by means of a French press, ultrasonication, a grinding mill treatment or a lysozyme treatment to obtain a crude solution of ω-carboxyalcohol oxidase. The solution is further treated by known isolation and purification methods for proteins and enzymes to obtain purified ω-carboxyalcohol oxidase. For example, the enzyme solution is treated with protamine sulfate to remove nucleic acids and is subjected to organic solvent precipitation by adding an organic solvent such as acetone, methanol, ethanol or isopropanol, or salting-out by adding ammonium sulfate, and chromatography using an ion-exchanger such as diethylaminoethyl cellulose or diethylaminoethyl Sepharose, or gel filtration chromatography using dextran gel or polyacrylamide gel. A purified enzyme powder can be obtained by combining the above procedures and finally lyophilizing the enzyme solution, with addition of one or more stabilizers such as BSA, gelatin, amino acid, sucrose, glycerin or ethyleneglycol.

An example of the assay method, as well as certain biochemical properties of the ω-carboxyalcohol oxidase of the present invention are as follows:

1. Assay Method

| | |
|---|---|
| 0.2 M Tris-HCl buffer (pH 7.5) | 0.20 ml |
| 10 mM 12-hydroxydodecanoic acid | 0.05 ml |
| 1% Triton X-100 | 0.05 ml |
| 0.2% phenol | 0.05 ml |
| 0.3% 4-aminoantipyrine | 0.05 ml |
| peroxidase (50 U/ml) | 0.05 ml |
| water | 0.05 ml |

An enzyme solution (25 μl) was added to the above mixture (0.5 ml), followed by incubation at 37° C. for exactly 10 mins., whereupon sodium dodecyl sulfate (SDS) (0.5 ml) was added thereto, then absorbance at 545 nm was measured. One unit of enzyme is defined by the activity which generates 1 μmole of hydrogen peroxide per minute.

2. Enzyme Action

1) A variation of an amount of aldehyde is measured by the following method.

Purified enzyme (0.3 unit) is added to a reaction mixture (0.5 ml) consisting of 0.2 M Tris-HCl buffer (pH 8.0) (0.2 ml), 10 mM 12-hydroxydodecanoic acid (0.01 ml), catalase (bovine liver, 20 units) and purified water (0.29 ml), followed by incubation at 37° C., whereafter 12% trichloroacetic acid (0.5 ml) was added after 5, 10, 20 and 40 mins. Then 0.1% 2,4-dinitrophenyl hydrazine (2N-HCl) was added thereto, and the resultant mixture was centrifuged at 3,000 rpm for 10 mins. The supernatant is boiled at 100° C. for 5 mins., cooled, 1.2N NaOH (3 ml) is added thereto and mixed well, then the absorbance is measured at 440 nm.

The results are shown in FIG. 1, in which generation and consumption of aldehyde is observed according to a process of reaction.

Figure 5:
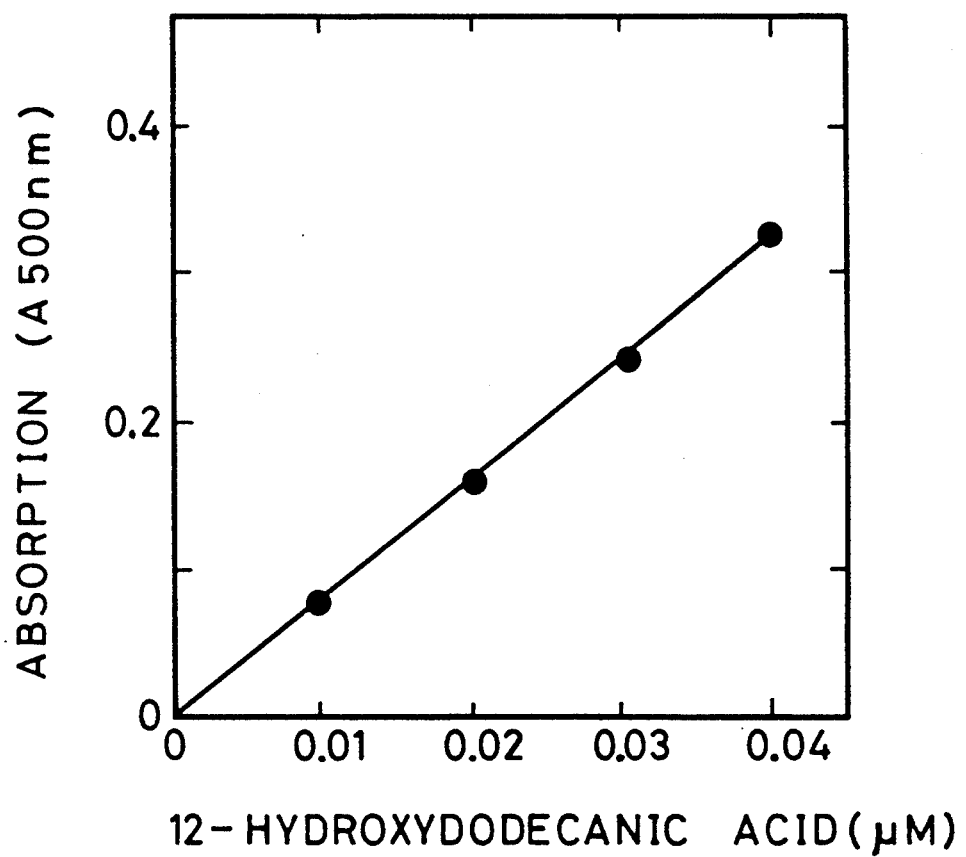
FIG. 5 is the standard curve for 12-hydroxydodecanoic acid.

2) As calculated from FIG. 5, two moles of hydrogen peroxide are generated from one mole of the substrate.

Accordingly, the enzyme of the present invention catalyzes at least one of the following reactions a) and b):

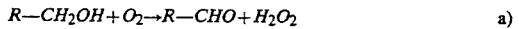

$$R-CH_2OH + O_2 \rightarrow R-CHO + H_2O_2 \qquad \text{a)}$$

$$R-CHO + O_2 + H_2O \rightarrow R-COOH + H_2O_2 \qquad \text{b)}$$

wherein $R-CH_2OH$ is an aliphatic alcohol or its ω-carboxylic acid derivative, except methanol and ethanol, $R-CHO$ is the corresponding aliphatic aldehyde or its ω-carboxylic acid derivative, and $R-COOH$ is the oxidized form of $R-CHO$.

The net reaction of the above two reactions a) and b) is thus:

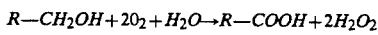

$$R-CH_2OH + 2O_2 + H_2O \rightarrow R-COOH + 2H_2O_2$$

Examples of aliphatic alcohols other than methanol and ethanol are for example, aliphatic alcohols over $C_3$.

3. Substrate Specificity

Substrate specificities of the enzyme are shown in Table 2. The enzyme has substrate specificity for at least $HO_2C-(CH_2)_{11}-OH$, $H_3C-(CH_2)_{11}-OH$, $H_3C-(CH_2)_9-OH$, $H_3C-(CH_2)_7-OH$ and $H_3C-(CH_2)_5-H$, and has no specificity on methanol, ethanol or glycerol.

Assay method: In the assay method illustrated at item 1. hereinabove, 12-hydroxydodecanoic acid was replaced by the substrates indicated in Table 2, and the resulting relative activities were produced, defining the activity on 12-hydroxydodecanoic acid as 100.

TABLE 2

| Substrate | Relative Activity (%) |
|---|---|
| $HO_2C-(CH_2)_{11}-OH$ | 100 |
| $HO_2C-(CH_2)_{15}-OH$ | 65.5 |
| $H_3C-(CH_2)_7-CH=CH-(CH_2)_8-OH$ | 59.1 |
| $H_3C-(CH_2)_{15}-OH$ | 60.2 |
| $H_3C-(CH_2)_{13}-OH$ | 76.1 |
| $H_3C-(CH_2)_{11}-OH$ | 86.1 |
| $H_3C-(CH_2)_9-OH$ | 87.6 |
| $H_3C-(CH_2)_7-OH$ | 88.5 |
| $H_3C-(CH_2)_5-OH$ | 88.5 |
| $H_3C-(CH_2)_3-OH$ | 76.1 |
| $H_3C-(CH_2)_2-OH$ | 6.6 |
| $H_3C-CH_2-OH$ | 0 |
| $H_3C-OH$ | 0 |
| glycerol | 0 |

As shown in Table 2, substrates for the enzyme of the present invention can be saturated or unsaturated aliphatic alcohols over $C_3$. When ω-carboxyalcohol such as $HO_2C-(CH_2)_{11}-OH$ and $HO_2C-(CH_2)_{15}-OH$ is used, the aldehyde $HO_2C-(CH_2)_{11}-CHO$ or $HO_2C-(CH_2)_{15}-CHO$, and finally the dicarboxylic acid $HO_2C-(CH_2)_{11}-CO_2H$ or $HO_2C-(CH_2)_{15}-CO_2H$ are generated.

4. Utilization of Coenzyme

No utilization of NAD and NADP is observed upon execution of the following assay method.

| Assay method | |
|---|---|
| 0.2 M Tris-HCl buffer (pH 7.5) | 0.5 ml |
| 10 mM NAD or NADP | 0.2 ml |
| 10 mM 12-hydroxydodecanoic acid | 0.2 ml |
| 1% Triton X-100 | 0.2 ml |
| water | 0.05 ml |

One unit of enzyme is added to the reaction mixture (2.0 ml) hereinabove and the absorbance at 340 nm and 37° C. is continuously measured.

The results are shown in Table 3, in which no increase in the absorption is observed, thereby indicating that the enzyme does not require NAD or NADP.

TABLE 3

| Time | $A_{340\ nm}$ | |
|---|---|---|
| | NAD | NADP |
| 0 min. | 0.062 | 0.046 |
| 2 mins. | 0.061 | 0.047 |
| 4 mins. | 0.060 | 0.045 |
| 6 mins. | 0.062 | 0.046 |
| 8 mins. | 0.061 | 0.046 |
| 10 mins. | 0.061 | 0.047 |

5. Molecular Weight

Approximately 66,000 (66,000±6,000), measured by gel-filtration method using Superose 12 column.

6. Optimum pH: pH 7.5±0.5

Optimum pH is measured according to the assay method illustrated at item 1. hereinbefore using the same component of reaction mixture, except that pH is varied.

Figure 2:
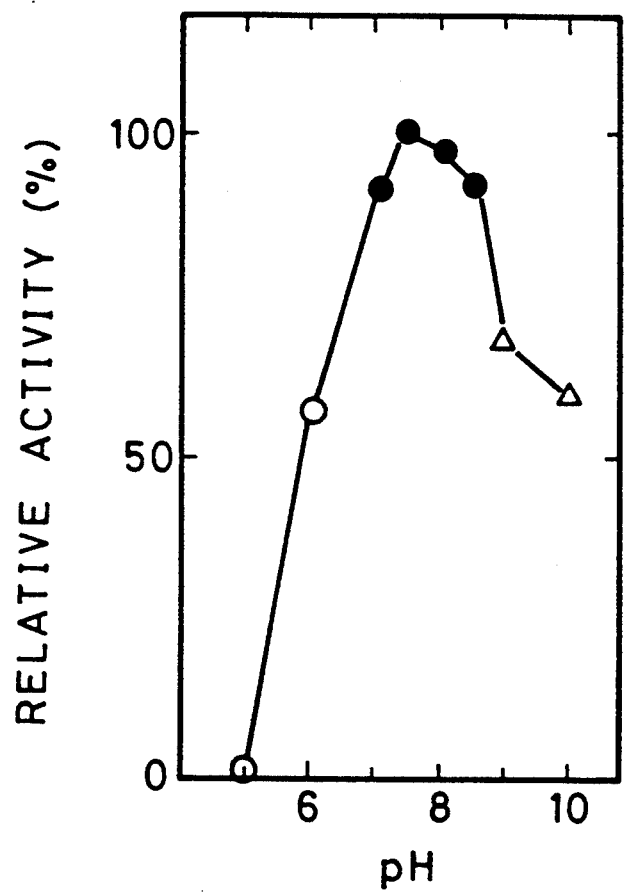
FIG. 2 shows the optimum pH range of the enzyme of the invention.

The results are shown in FIG. 2. In FIG. 2:

○: MES-buffer,
●: Tris-HCl buffer,
△: glycine-NaOH buffer.

7. Stable pH-range: pH 6-9.

Stable pH-range of the enzyme in various buffer solutions is measured by dissolving the enzyme in 10 mM buffer, the resulting solution being heated at 37° C. for 60 mins. and immediately cooled, and the remaining activities measured at each pH.

Figure 3:
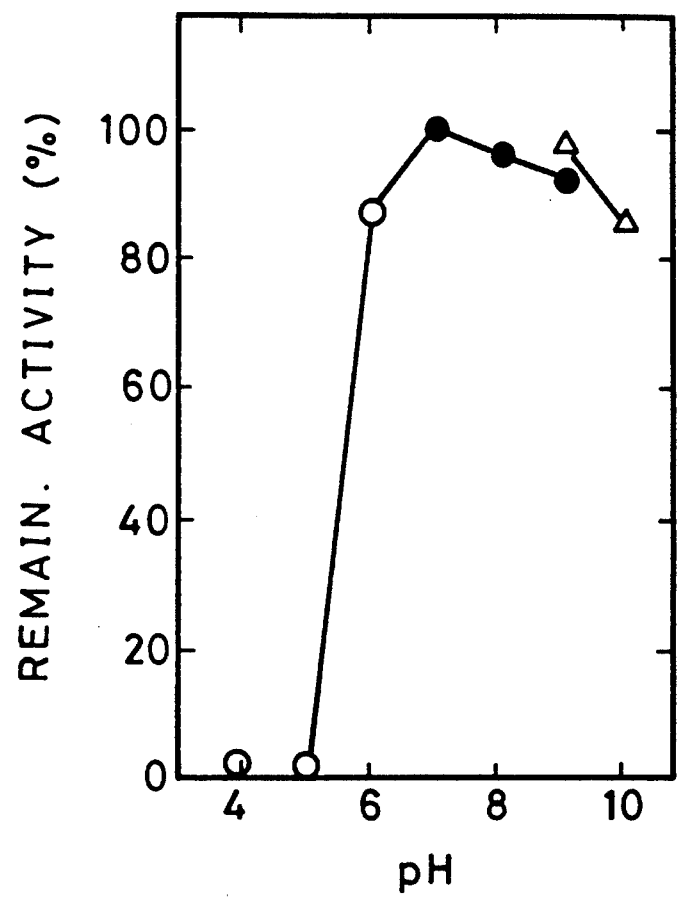
FIG. 3 shows the stable pH range of the enzyme.

The results are shown in FIG. 3, in which:
○: MES-buffer,
●: Tris-HCl buffer,
△: glycine-NaOH buffer.

8. Heat stability: stable at 45° C. and pH 7.5, for a duration of at least 10 mins.

The enzyme, dissolved in 0.1 M Tris-HCl buffer (pH 7.5), is incubated at various temperatures for 10 mins and immediately cooled, with the remaining activities being measured.

Figure 4:
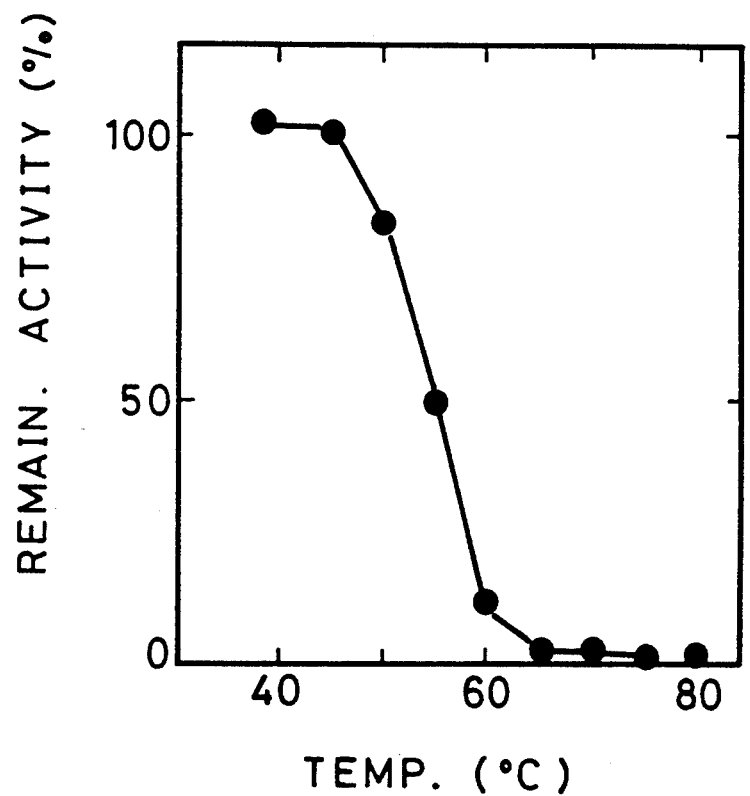
FIG. 4 shows the heat stability of the enzyme.

The results are shown in FIG. 4.

9. Effects of Reagents

The effects of various detergent and metal ions are shown in Table 4, in which the listed reagents show no significant effect on the enzyme. Activities of the enzyme are measured by adding each listed detergent and metal ion to the assay method described above at item 1.

TABLE 4

| Reagent | Concentration | Relative Activity (%) |
|---|---|---|
| None | | 100 |
| NaCl | 100 mM | 95.1 |
| KCl | 100 mM | 97.6 |
| NH_4Cl | 100 mM | 89.0 |
| CaCl | 1 mM | 97.0 |
| MgCl_2 | 1 mM | 98.2 |
| MnCl_2 | 1 mM | 102.4 |
| Triton X-100 | 1.0% | 93.1 |
| Deoxycholate | 10 mM | 94.9 |
| Cholate | 10 mM | 94.9 |

10. Isoelectric point: pH 4.5±0.2 (isoelectric focusing using carrier ampholyte).

The present invention also includes a method for detecting aliphatic alcohol, aliphatic aldehyde or ω-carboxylic acid derivatives thereof, comprising reacting in an aqueous medium a sample containing a compound of the formula, R'—CH_2OH or R'—CHO, wherein R'—CH_2 OH is an aliphatic alcohol other than methanol and ethanol, or its ω-carboxylic acid derivative, and R'—CHO is the corresponding aliphatic aldehyde or its ω-carboxylic acid derivative; with ω-carboxyalcohol oxidase having the following biochemical properties:

1) Enzyme action: catalyzing at least one of the following reactions a) and b)

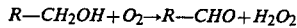

$$R-CH_2OH+O_2 \rightarrow R-CHO+H_2O_2 \qquad \text{a)}$$

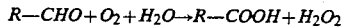

$$R-CHO+O_2+H_2O \rightarrow R-COOH+H_2O_2 \qquad \text{b)}$$

wherein R—CH_2OH is an aliphatic alcohol or its ω-carboxylic acid derivative, except methanol and ethanol, R—CHO is the corresponding aliphatic aldehyde or its ω-carboxylic acid derivative, and R—COOH is the oxidized form of R—CHO.

2) Substrate specificity: having substrate specificity on at least $HO_2C-(CH_2)_{11}-OH$, $H_3C-(CH_2)_{11}-OH$, $H_3C-(CH_2)_9-OH$, $H_3C-(CH_2)_7-OH$ and $H_3C-(CH_2)_5-OH$, and having no substrate specificity on methanol, ethanol or glycerol.

3) Utilization of coenzyme: no utilization of NAD or NADP.

The ω-carboxyalcohol oxidase used in the method of the present invention has the biochemical properties shown hereinabove. The preferred enzyme for production of ω-carboxyalcohol oxidase is Streptomyces sp. AC 8205.

R′—CH$_2$OH in a specimen is an aliphatic alcohol (except methanol and ethanol) or its ω-carboxylic acid derivative. For example, it can be a long chain alcohol of more than C$_3$, such as HO$_2$C—(CH$_2$)$_{11}$—OH, HO$_2$C—(CH$_2$)$_{15}$—OH, H$_3$C—(CH$_2$)$_7$—CH=CH—(CH$_2$)$_8$—OH, H$_3$C—(CH$_2$)$_{15}$—OH, H$_3$C—(CH$_2$)$_{13}$—OH, H$_3$C—(CH$_2$)$_3$—OH and H$_3$C—(CH$_2$)$_2$—OH. Among these, HO$_2$C—(CH$_2$)$_{11}$—OH, H$_3$C—(CH$_2$)$_{11}$—OH, H$_3$C—(CH$_2$)$_9$—OH, H$_3$C—(CH$_2$)$_7$—OH and H$_3$C—(CH$_2$)$_5$—OH are preferred. R′—CHO in the specimen can be an aliphatic aldehyde (except formaldehyde and acetaldehyde) or its ω-carboxylic acid derivative, for example the aldehyde compounds corresponding to the above aliphatic alcohols or their ω-carboxylic acid derivatives.

The concentration of R′—CH$_2$OH or R′—CHO in a specimen is usually 0.01-0.05 mM and may be diluted or subjected to pretreatment. Reaction temperature is generally approximately 0°-40° C. The amount of ω-carboxyalcohol oxidase used is approximately 1-10 units.

The components consumed in the reaction are substrate, oxygen and water. The generated components are R′—CHO, R′—COOH and H$_2$O$_2$. The increase or decrease in amount of any of these component may be measured to effect the assay.

In an assay, any proper method can be used. For example, if generated H$_2$O$_2$ is measured, then the peroxidase method can be applied. Known chromogen, coloring reagent, luminescent reagent and fluorescence reagent are reacted with generated H$_2$O$_2$ in the presence of peroxidase and absorbance of the reaction mixture is measured.

R′—CH$_2$OH or R′—CHO can be a component in the specimen as it is or it can be a component generated from the corresponding aliphatic ester by an action of esterase or lipase.

The present invention further includes a process for production of a carboxylic acid which comprises contacting in an aqueous medium R″—CH$_2$OH or R″—CHO, wherein R″—CH$_2$OH is an aliphatic alcohol (except methanol and ethanol) or its ω-carboxylic acid derivative, R″—CHO is a corresponding aliphatic aldehyde or its ω-carboxylic acid derivatives, and R″—CH$_2$OH or R″—CHO is also a substrate for ω-carboxyalcohol oxidase; with a substrate which can produce carboxylic acid, in the presence of ω-carboxyalcohol oxidase having the following biochemical properties:

1. Enzymatic action: catalyzing at least one of the following reactions a) and b)

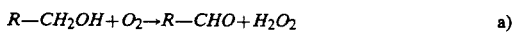

$$R—CH_2OH + O_2 \rightarrow R—CHO + H_2O_2 \quad \text{a)}$$

$$R—CHO + O_2 + H_2O \rightarrow R—COOH + H_2O_2 \quad \text{b)}$$

wherein R—CH$_2$OH is an aliphatic alcohol (except methanol and ethanol) or its ω-carboxylic acid derivative, R—CHO is a corresponding aliphatic aldehyde or its ω-carboxylic acid derivative, and R—COOH is the oxidized form of R—CHO.

2. Substrate specificity: having substrate specificity on at least HO$_2$C—(CH$_2$)$_{11}$—OH, H$_3$C—(CH$_2$)$_{11}$—OH, H$_3$C—(CH$_2$)$_9$—OH, H$_3$C—(CH$_2$)$_7$—OH and H$_3$C—(CH$_2$)$_5$—OH, and having no substrate specificity on methanol, ethanol or glycerol.

3. Utilization of coenzyme: no utilization of NAD and NADP.

The ω-carboxyalcohol oxidase used in the process for production of carboxylic acid according to the present invention may be any enzyme which has the biochemical properties shown hereinbefore. The preferred enzyme is ω-carboxyalcohol oxidase produced by Streptomyces sp. AC 8205.

The substrate R″—CH$_2$OH is aliphatic alcohol (except methanol and ethanol) or its ω-carboxylic acid derivative. For example, it can be a long chain alcohol of more than C$_3$, such as HO$_2$C—(CH$_2$)$_{11}$—OH, HO$_2$C—(CH$_2$)$_{15}$—OH, H$_3$C—(CH$_2$)$_7$—CH=CH—(CH$_2$)$_8$—OH, H$_3$C—(CH$_2$)$_{15}$—OH, H$_3$C—(CH$_2$)$_{13}$—OH, H$_3$C—(CH$_2$)$_{11}$—OH, H$_3$C—(CH$_2$)$_9$—OH, H$_3$C—(CH$_2$)$_7$—OH, H$_3$C—(CH$_2$)$_5$—OH, H$_3$C—(CH$_2$)$_3$—OH or H$_3$C—(CH$_2$)$_2$—OH. Among these, HO$_2$C—(CH$_2$)$_{11}$—OH, H$_3$C—(CH$_2$)$_{11}$—OH, H$_3$C—(CH$_2$)$_9$—OH, H$_3$C—(CH$_2$)$_7$—OH and H$_3$C—(CH$_2$)$_5$—OH are preferred. The substrate R″—CHO can be an aliphatic aldehyde (except formaldehyde and acetaldehyde) or its ω-carboxylic acid derivative, for example the aldehyde compound corresponding to the above aliphatic alcohol or its ω-carboxylic acid derivative.

The concentration of the substrate in the production process is, for example, 10-500 μM.

The aqueous medium is not particularly limited in that it is a medium which contains water and has no detrimental effect on the enzymatic reaction. Examples thereof are aqueous media such as water or buffer solution, and a mixed solvent with water and organic solvent. Examples of organic solvent are methanol, ethanol, propanol or butanol, or acetone or mixture thereof. Preferred examples are aqueous methanol, aqueous ethanol, aqueous acetone or chloroform.

Oxygen can be supplied by bubbling oxygen gas, or if the amount of substrate is very small, dissolved oxygen in an aqueous medium can be used for reaction.

In the production of carboxylic acid, ω-carboxyalcohol oxidase of the present invention can be prepared as an immobilized enzyme on a carrier.

Immobilization can be effected by a known method, for example a carrier binding method (binding with insoluble carrier by covalent bond, ionic bond or adsorption), cross linkage method or encapsulating method (lattice type polymer gel, microcapsule or hole fiber) or a combination thereof. The preferred method is the covalent bond method or adsorption method.

Examples of carriers are natural polymers, synthetic polymers and inorganic materials, such as cellulose, agarose, dextran, chitin, collagen, tannin, fibrin, albumin, casein, carrageenan, amino acid polymers, polystyrene, sulfonated polystyrene, carboxylated polystyrene, aminated polystyrene; copolymers of substituted or unsubstituted styrene derivative monomer and methylstyrene, ethylstyrene, chlorosytrene, ethylene, propylene, acrylic acid, acrylic acid methyl ester, acrylic acid ethyl ester, methacrylic acid, methacrylic acid methyl ester, methacrylic acid ethyl ester, acrylonitrile, acrylamide, maleic acid, fumaric acid, butadiene, chloroprene, isoprene, vinylchloride, vinylidene chloride, vinylacetate, vinyl toluene or divinyl benzene; polyvinyl toluene, polyester, polyacrylate, polymethacrylate, polyacrylonitrile, aminated polyacrylonitrile, polyvinylpyrrolidone, polyacetate vinylacrylate and vinyl-chloride-acrylate copolymer.

Examples of crosslinking reagent are glutaraldehyde, hexamethylene diisocyanate, toluene diisocyanate, xylene diisocyanate, dialdehyde starch, dimethyladipidate, dimethylsulbelimidate and dimethyl-3,3'-dithiobis-propionimidate.

The carrier surface may be previously activated with hydrazine, thionylchloride, carbodiimide, phosgen, ethylene chloroformate or bromcyanide.

The forms of the carrier may be selected according to the type of operation, from pellet, granule, film, sheet, fiber or gel types.

The reaction temperature is a temperature which does not denature the enzyme, for example approximately 10°–40° C. Reaction time can be selected according to the conditions such as amount of enzyme used, and it can be determined by checking the reaction process using TLC.

The amount of enzyme activity used in the reaction is generally 1–10 units.

An ω-dibasic acid, which is useful as a starting material of plastics and lubricants, can be produced from substrates such as ω-carboxylic acid derivative of aliphatic alcohol or ω-carboxylic acid derivative of aliphatic aldehyde. The enzymatic process of the present invention is of economic advantage as compared with chemical synthesis.

EXAMPLES

The following examples illustrate the present invention but are not to be construed as limiting.

EXAMPLE 1

20 l of a pH 7.0 aqueous medium comprising 1% peptone, 1% fish meat extract, 2% fructose, 0.3% NaCl, 0.3% $KH_2PO_4$, 0.3% $MgSO_4$ and 0.2% antifoaming reagent Disform BC-51Y was sterilized at 120° C. for 20 mins. 200 ml of a seed culture of Streptomyces sp. AC 8205 FERM BP-2491 cultured previously in the same medium was inoculated into the above medium and submerged cultured at 28° C. for 55 hours, with aseptic aeration of 20 l/min. and 300 rpm agitation (0.01 U/ml).

The cultured broth (17 l) was separated centrifugally at 5,000 rpm for 10 mins. and the obtained cells were suspended in 8 l of pH 7.0 10 mM phosphate buffer containing 0.1% Triton X-100 and 1 mg/ml lysozyme, then autolysated at 37° C. for two hours. The mixture was centrifuged at 5,000 rpm for 10 mins. to obtain crude enzyme extract solution (7.8 l). Acetone (2-fold volumes) was added thereto and the precipitate was dissolved in 10 mM phosphate buffer (pH 7.0) containing 20% ammonium sulfate.

Insoluble material was removed by centrifugation at 12,000 rpm for 10 mins. The supernatant solution (490 ml) was charged on an octyl-Sepharose CL-6B column (2.6×10 cm) to adsorb the enzyme. Then the column was subjected to elution with 300 ml 15% ammonium sulfate solution and 300 ml 10% ammonium sulfate solution, and the active fractions measured according to the assay method, i.e. 300 ml fractions eluted by 10% ammonium sulfate were collected and dialyzed in a cellulose acetate tube against 10 mM Tris-HCl buffer (pH 7.5, 5 lit.) at 4° C. for 15 hours. The dialyzate was lyophilized to obtain purified ω-carboxyalcohol oxidase (155 mg, 0.3 U/mg).

EXAMPLE 2

Assaying ω-carboxylic acid of aliphatic alcohol

| | |
|---|---|
| 0.2 M Tris-HCl buffer (pH 8.0) | 0.5 ml |
| 0.3% 4-aminoantipyrine | 0.3 ml |
| 0.2% phenol | 0.3 ml |
| peroxidase (45 U/ml) | 0.2 ml |
| ω-carboxyalcohol oxidase (5 U/ml) | 0.1 ml |
| water | 0.6 ml |

12-hydroxydodecanoic acid (20 μl) was added to the above reaction mixture, followed by incubation at 37° C. for 10 mins., whereupon the absorbency at 500 nm was measured.

The results are shown in FIG. 3, from which it can be seen that a good standard curve was obtained.

EXAMPLE 3

Production of Dibasic Acid

The enzyme produced in Example 1 was dissolved in 0.2M PIPES-NaOH buffer (pH 7.3, 0.5 ml). The resultant enzyme solution (2U) and catalase (bovine liver, 5U) were added to 12-hydroxydodecanoic acid (100 mg) dissolved in acetone (10 ml) and the ensuing mixture was reacted at 28° C. for 18 hours.

The reaction mixture was then dried in vacuo and the residue was mixed with 5 ml chloroform-methanol (2:1) and 2 ml water. The chloroform layer was dried to obtain 75 mg of the dibasic acid 1,12-dodecane dicarboxylic acid.

TLC: Rf =approx. 0.8 (silica gel 60 plate, developer: chloroform-methanol-acetone (80:20:5), detection: 0.03% methyl red-95% ethanol solution)

EXAMPLE 4

In Example 3, acetone solution of 12-hydroxydodecanoic acid was replaced by 16-hydroxy hexadecanoic acid (100 mg) dissolved in chloroform (10 ml) and reaction time was set for 15 hours. 72 mg of 1,16-hexadecane dicarboxylic acid was produced.

EXAMPLE 5

Production of carboxylic acid using immobilized enzyme:

1. Immobilization of the Enzyme

Aminated polyacrylonitrile fiber (2.0 g, wet weight) was treated with 25% glutaraldehyde at 0° C. for 1 hour, filtered with glass filter and washed with purified water (200 ml).

The enzyme (25 ml, 30 units) dissolved in 1M phosphate buffer (pH 7.0) was contacted with the fiber, stirred at 30° C. for 30 mins., filtered with glass filter, and washed with 50 ml of 10 mM Tris-HCl buffer to obtain 2.1 g of the immobilized enzyme.

Immobilization ratio: 73%

Activity expressed: 67%

2. Production of carboxylic acid with immobilized enzyme system:

Immobilized enzyme (200 mg) obtained in step 1. hereinabove was used under the same conditions as in Example 4. Dibasic acid, 1,16-hexadecane dicarboxylic acid (80 mg) was produced.

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. A process for producing carboxylic acids higher than $C_3$, comprising contacting in an aqueous medium and in the presence of oxygen 1) R"—$CO_2OH$ or R"—CHO, wherein R"—$CH_2OH$ is an aliphatic alcohol higher than $C_3$, or its ω-carboxylic acid derivative, R"—CHO is a corresponding aliphatic aldehyde higher than $C_3$ or its ω-carboxylic acid derivative, and 2) isolated and purified ω-carboxy-alcohol oxidase having the following biochemical properties:

enzymatic action: catalyzing both of the following reactions a) and b)

$$R-CH_2OH + O_2 \rightarrow R-CHO + H_2O_2 \qquad \text{a)}$$

$$R-CHO + O_2 + H_2O \rightarrow R-COOH + H_2O_2 \qquad \text{b)}$$

wherein R—$CH_2OH$ is an aliphatic alcohol higher than $C_3$ or its ω-carboxylic acid derivative, R—CHO is a corresponding aliphatic aldehyde higher than $C_3$ or its ω-carboxylic acid derivative, and R—COOH is the oxidized form of a R—CHO;

substrate specificity: having substrate specificity on at least $HO_2C-(CH_2)_{11}-OH$, $H_3C-(CH_2)_{11}-OH$, $H_3C-(CH_2)_9-OH$, $H_3C-(CH_2)_7-OH$ and $H_3C-(CH_2)_5-OH$, and having no substrate specificity on methanol, ethanol or glycerol; and utilization of coenzyme: no utilization of NAD or NADP.

2. The process according to claim 1 wherein the ω-carboxyalcohol oxidase further comprises the following properties:

molecular weight: 66,000±6,000
optimum pH; 7.5±0.5
stable pH range: pH 6–9
heat stability: stable at 45° C. and pH 7.5 for at least 10 minutes.